(12) United States Patent
Atwell

(10) Patent No.: US 9,023,041 B2
(45) Date of Patent: May 5, 2015

(54) ELECTROSURGICAL INSTRUMENT INCLUDING A RETRACTABLE AND SELECTIVELY ACTIVATED ELECTRODE ASSEMBLY

(75) Inventor: Anthony K. Atwell, Newport (GB)

(73) Assignee: Gyrus Medical Limited, Cardiff (GB)

( * ) Notice: Subject to any disclaimer, the term of this patent is extended or adjusted under 35 U.S.C. 154(b) by 383 days.

(21) Appl. No.: 13/485,170

(22) Filed: May 31, 2012

(65) Prior Publication Data

US 2012/0323231 A1    Dec. 20, 2012

(30) Foreign Application Priority Data

Jun. 15, 2011 (GB) .................................. 1110108.6

(51) Int. Cl.
*A61B 18/14* (2006.01)
*A61B 18/00* (2006.01)

(52) U.S. Cl.
CPC ... *A61B 18/1477* (2013.01); *A61B 2018/00607* (2013.01); *A61B 2018/1475* (2013.01)

(58) Field of Classification Search
USPC ......................................... 606/45–46, 48–50
See application file for complete search history.

(56) References Cited

U.S. PATENT DOCUMENTS

| | | | |
|---|---|---|---|
| 5,071,419 A * | 12/1991 | Rydell et al. | 606/48 |
| 6,666,864 B2 * | 12/2003 | Bencini et al. | 606/41 |
| 7,648,501 B2 | 1/2010 | Durgin et al. | |
| 2003/0040744 A1 | 2/2003 | Latterell et al. | |
| 2003/0163123 A1 | 8/2003 | Goble et al. | |
| 2005/0283149 A1 * | 12/2005 | Thorne et al. | 606/48 |

OTHER PUBLICATIONS

British Search Report issued in Application No. 1110108.6; Dated Oct. 11, 2011.

* cited by examiner

*Primary Examiner* — Paula J Stice
(74) *Attorney, Agent, or Firm* — Oliff PLC

(57) ABSTRACT

An electrosurgical instrument includes an instrument shaft having a longitudinal axis, and an electrode assembly at one end of the shaft, the electrode assembly including first, second and third electrodes which are electrically insulated one from another by means of one or more insulation members. The instrument further includes first and second connections by which RF energy can be supplied to the instrument from an electrosurgical generator. The first electrode is movable longitudinally between an advanced position in which it extends from the instrument shaft and a retracted position in which it is less advanced with respect to the instrument shaft. When the first electrode is in its advanced position, the first and second connections are in electrical communication with the first and second electrodes. When moved to its retracted position, the first and second connections are caused to be in electrical communication with the second and third electrodes.

17 Claims, 3 Drawing Sheets

ELECTROSURGICAL INSTRUMENT INCLUDING A RETRACTABLE AND SELECTIVELY ACTIVATED ELECTRODE ASSEMBLY

FIELD OF THE INVENTION

This invention relates to an electrosurgical instrument for the treatment of tissue.

BACKGROUND OF THE INVENTION

Electrosurgical instruments are commonly used for the cutting/vaporisation and/or desiccation/coagulation of tissue in surgical intervention, most commonly in "keyhole" or minimally invasive surgery. The terms "cutting" and "vaporization" relate to the removal of tissue, whether by resection or by the volumetric removal of tissue. Similarly, the terms "desiccation" and "coagulation" relate to the creation of lesions in tissue, the necrosis of tissue, and to the prevention of bleeding.

Endoscopic instruments are often used in gastroenterology or cardiac surgery, and such instruments are normally introduced through a lumen within the patient's body. These instruments are therefore of a relatively small size, often no more than 5 mm in diameter. They are deployed at the end of a relatively long flexible shaft, such that they can be manoeuvred within a lumen as described above.

One instrument of this type is described in U.S. Pat. No. 7,648,501. It includes a cutting electrode deployable from the end of a catheter, and coagulation electrodes present on the instrument tip surrounding the cutting electrode. The present invention attempts to provide an improvement to endoscopic instruments of this type.

SUMMARY OF THE INVENTION

According to this invention, an electrosurgical instrument is provided for the treatment of tissue, the instrument comprising an instrument shaft having a longitudinal axis, and an electrode assembly at one end of the shaft, the electrode assembly comprising first, second and third electrodes which are electrically insulated one from another by means of one or more insulation members, the instrument further comprising first and second connections by which RF energy can be supplied to the instrument from an electrosurgical generator, the first electrode being movable longitudinally between an advanced position in which it extends from the instrument shaft and a retracted position in which it is less advanced with respect to the instrument shaft, the arrangement being such that when the first electrode is in its advanced position the first and second connections are in electrical communication with the first and second electrodes, and such that the movement of the first electrode to its retracted position causes the first and second connections to be in electrical communication with the second and third electrodes.

The term "instrument shaft" is hereby meant to include not only a rigid shaft common in laparoscopic instruments, but also a flexible tube used in endoluminal surgery. Depending on the position of the first electrode, the electrical connections are connected to different pairs of electrodes. Unlike U.S. Pat. No. 7,648,501, which requires separate electrical leads for each of the three electrodes, the present invention therefore provides an instrument requiring only two leads, which can greatly simplify the design and manufacture of the instrument, bearing in mind that the flexible shaft may extend over a meter in length.

When the first electrode is in its advanced position, the first connection is preferably in electrical communication with the first electrode and the second connection is in electrical communication with the second electrode. Similarly, when the first electrode is in its retracted position, the first connection is preferably in electrical communication with the third electrode and the second connection is in electrical communication with the second electrode.

The first electrode is preferably adapted to perform electrosurgical cutting of tissue, and is typically in the form of a needle electrode. The first electrode is conveniently located in a lumen extending longitudinally through the electrosurgical instrument, and can be advanced and retracted within the lumen. In this way, the first electrode can either be advanced to extend from the lumen, or be retracted into a less advanced position. Normally, the advanced position will be adopted when electrosurgical cutting is required, and the less advanced position when electrosurgical coagulation is required. Preferably, the first electrode is such that it is completely contained within the instrument shaft when in its retracted position, but conceivably the less advanced position may still see the first electrode projecting from the lumen, albeit to a lesser extent than before.

The second and third electrodes are conveniently adapted to perform electrosurgical coagulation of tissue. According to a preferred configuration the second and third electrodes comprise first and second printed patterns present on the annular body. In this arrangement, the annular body is formed from an electrically insulating material, and forms the substrate on which the first and second printed patterns are formed. In this arrangement, electrosurgical cutting takes place between the first and second electrodes, i.e. the needle electrode and one of the printed patterns formed on the annular body. Electrosurgical coagulation takes place between the second and third electrodes, i.e. the first and second printed patterns formed on the annular body.

Alternatively, the instrument includes an annular body surrounding the first electrode. This annular body is conveniently electrically conductive and constitutes the third electrode. In this arrangement, the second electrode conveniently comprises an electrically conductive layer on at least part of the annular body, an electrically insulating layer being present between the annular body and the conductive layer. In this way, electrosurgical cutting takes place between the first and second electrodes, i.e. the needle electrode and the electrically conductive layer covering the annular body. Electrosurgical coagulation takes place between the second and third electrodes, i.e. the conductive layer covering the annular body and the annular body itself, across the insulating layer separating the conductive layer from the annular body.

The instrument preferably includes first and second electrical contacts, the first contact being in electrical connection with the first electrode and the second contact being in electrical connection with the third electrode. The first contact is conveniently carried on the first electrode, and the first and second contacts are such that they are not in contact when the first electrode is in its advanced position. Thus, when the first electrode is in its advanced position, the first and second contacts are separated one from another, and the electrical connections supply energy from the generator between the first and second electrodes, i.e. for electrosurgical cutting of tissue. Preferably, the first and second contacts are such that they are in contact when the first electrode is in its retracted position. Thus when the first electrode is in its retracted position, the first and second contacts are in contact one with another, electrically connecting the first and third electrodes. In this position, the electrical connections supply energy from the generator between the second and third electrodes, i.e. for electrosurgical coagulation of tissue. If the first electrode is not entirely withdrawn within the annular body, it can also act to coagulate tissue, although coagulation will primarily be performed between the second and third electrodes, of whichever configuration.

The electrode assembly is typically such that the second and third electrodes are mounted on a unitary body, but other arrangements are equally possible. For example, the second and third electrodes could conceivably be mounted on movable jaws, which can be opened and closed in order to grasp tissue therebetween. In one arrangement, first and second jaw members actually constitute the second and third electrodes.

The invention also provides an electrosurgical instrument for the treatment of tissue, the instrument comprising an instrument shaft having a longitudinal axis, and an electrode assembly at one end of the shaft, the electrode assembly comprising first, second and third electrodes which are electrically insulated one from another by means of one or more insulation members, the instrument further comprising first and second connections by which RF energy can be supplied to the instrument from an electrosurgical generator, the first electrode being movable longitudinally between an advanced position in which it extends from the instrument shaft and a retracted position in which it is less advanced with respect to the instrument shaft, wherein the instrument further comprises, associated with the distal end of the instrument shaft, a pair of electrical coupling elements the relative position of which is caused to alter by movement of the first electrode between its advanced and retracted positions thereby to form an electrical coupling such that when the first electrode is in its advanced position the first and second connections are in electrical communication with the first and second electrodes, and when the first electrode is in its retracted position the first and second connections are in electrical communication with the second and third electrodes. In the preferred embodiment of the invention, both the first electrode and the third electrode each have respective electrical contacts forming the coupling elements, which contacts engage each other when the first electrode is retracted. Typically, the coupling elements comprise a first coupling element located on the first electrode and coupled to the said first connection, and a second coupling element located adjacent the first electrode and coupled to the third electrode, the relative positions of the coupling elements being such that movement of the first electrode to its retracted position brings the coupling elements together thereby to form an electrical path between the first connection and the third electrode.

The invention is further described below, by way of example only, with reference to the accompanying drawings.

DETAILED DESCRIPTION OF PREFERRED EMBODIMENTS OF THE INVENTION

Figure 1:
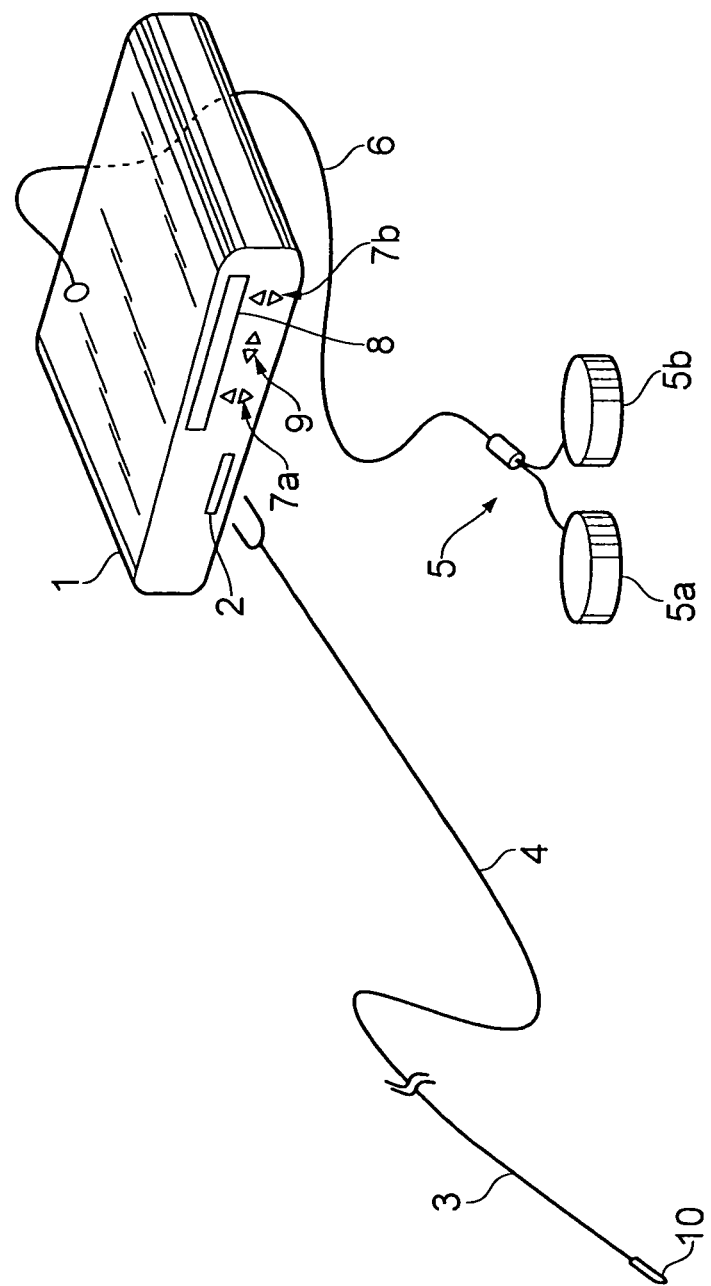
FIG. 1 is a schematic diagram of an electrosurgical system including an electrosurgical instrument in accordance with the present invention.

Referring to the drawings, FIG. 1 shows electrosurgical apparatus including a generator 1 having an output socket 2 providing a radio frequency (RF) output, via a connection cord 4, for an instrument 10 at the end of a flexible sheath 3. Activation of the generator 1 may be performed by means of a footswitch unit 5 connected separately to the rear of the generator 1 by a footswitch connection cord 6. In the illustrated embodiment, the footswitch unit 5 has two footswitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9 are provided as an alternative means for selection between the desiccation and vaporisation modes.

Figure 2:
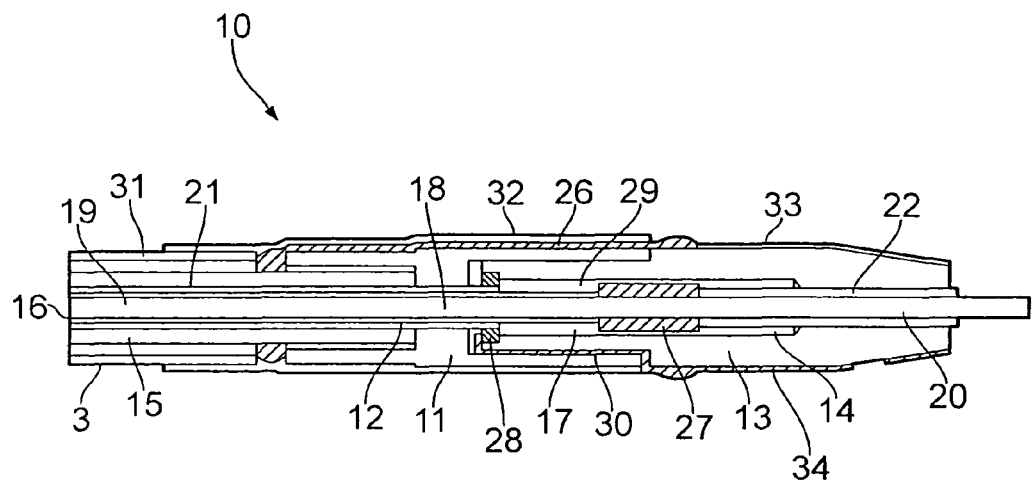
FIG. 2 is a sectional side view of an electrosurgical instrument in accordance with the present invention shown in its extended position.

FIG. 2 shows the instrument 10 in more detail. The instrument is based around an insulating body member 11 having a lumen 12 running therethrough. Distal of the body member 11 is an annular body 13, formed of an insulating material such as ceramic, also with a lumen 14 running therethrough. Proximal of the body member 11 is the flexible sheath 3, which comprises a flexible conductive tube 15, which also has a lumen 16 running therethrough. The lumens 12, 14 & 16 are aligned and contiguous so as to form a single lumen 17 running through the instrument 10.

Present within the lumen 17 is a longitudinally movable electrode assembly 18. The electrode assembly comprises a conductive guide wire 19 terminating in a first electrode in the form of a needle electrode 20. The guide wire 19 is covered with an insulating covering 21 to insulate the guide wire from the conductive tube 15. Further insulation 31 covers the external surface of the conductive tube 15. The distal end of the needle electrode 20 lies within a guide tube 22, typically also of a ceramic material, to guide the electrode 20 in and out of the annular body 13.

The external surface of the insulating annular body 13 is provided on its surface with two separate printed patterns 33 & 34, the printed patterns being formed of an electrically conductive ink so as to form second and third electrodes. The electrical connections for the patterns 33 & 34 will be described shortly.

The instrument 10 is connected to the electrosurgical generator 1, with the guide wire 19 acting as one electrical connection and the flexible conductive tube 15 active as the second electrical connection. The guide wire 19 is electrically connected to the needle electrode 20, while a lead 26 covered by an insulating layer 32 runs from the conductive tube 15 to one of the electrode patterns 33. Thus, when the needle electrode 20 is in its advanced position as shown in FIG. 2, the RF energy from the generator is supplied between the needle electrode 20 and the conductive pattern 33, allowing the needle to perform the electrosurgical cutting of tissue adjacent thereto.

Figure 3:
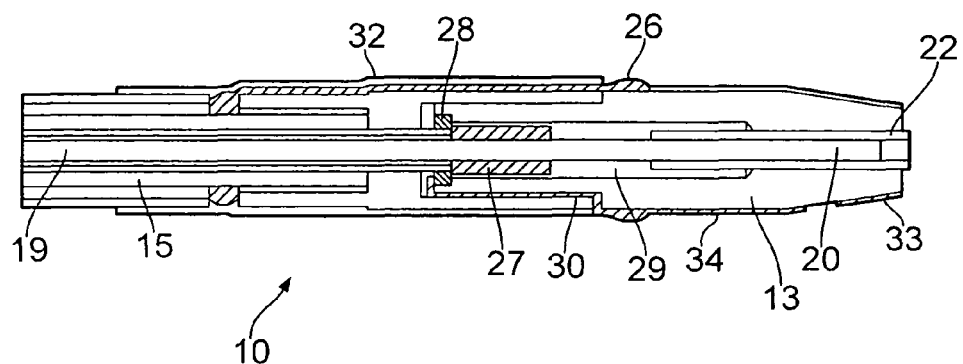
FIG. 3 is a sectional side view of the electrosurgical instrument of FIG. 2 shown in its retracted position.

A first contact is present on the electrode assembly 18, at the junction between the guide wire 19 and the needle electrode 20. The contact is in the form of a conductive bushing 27 present between the insulating covering 21 on the guide wire and the guide tube 22 for the needle electrode. A second contact in the form of an annular ring 28 is present at the proximal end of the annular body 13 and extending into the lumen 17. The conductive bushing 27 is accommodated by a widening of the lumen 17 to form a chamber 29. The annular ring 28 is in electrical contact with the second pattern 34 via lead 30. When the needle electrode is retracted back from its advanced position by the operation of a remote handle (not shown) the conductive bushing 27 comes into contact with the annular ring 28, as shown in FIG. 3. This means that RF energy from the generator 1 is directed from the guide wire 19, through the conductive bushing 27 and annular ring 28 to the second pattern 34. The RF energy from the generator is supplied between the first and second patterns 33 & 34, allowing the instrument to perform the electrosurgical coagulation of tissue adjacent thereto. The first and second printed patterns 33 & 34 can be of different configurations, as long as they do not contact one another. The patterns can be interlocking shapes or fingers, or merely two separate sections on the surface of the annular body 13.

Figure 4:
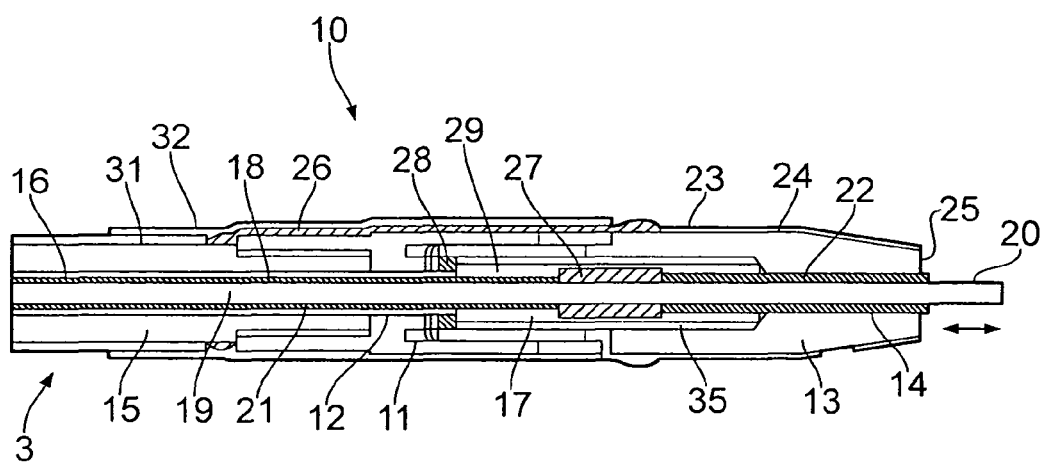
FIG. 4 is a sectional side view of an alternative embodiment of electrosurgical instrument in accordance with the present invention.

FIG. 4 shows an alternative embodiment of instrument 10, which is similar to that shown in FIGS. 2 & 3 such that similar components are designated with similar reference numerals. The key difference is that the annular body 13 is formed of a conductive material, such as stainless steel. The guide tube 22 is formed of an insulating material such as ceramic, in order to insulate the needle electrode 20 from the conductive annular body 13.

The external surface of the conductive annular body 13 is provided with a conductive coating 23, the annular body being provided with an insulating layer 24 to separate the coating 23 from the annular body 13. The insulating layer does not extend around the end of the annular body 13, leaving the end face 25 exposed, although in other embodiments the coating and insulating layer could extend around at least part of the end face 25. The conductive coating therefore constitutes the second electrode, while the annular body itself constitutes the third electrode, as will be explained in more detail hereafter.

The instrument 10 is connected to the electrosurgical generator 1, with the guide wire 19 acting as one electrical connection and the flexible conductive tube 15 active as the second electrical connection as before. The guide wire 19 is electrically connected to the needle electrode 20, while the lead 26 covered by an insulating layer 32 runs from the conductive tube 15 to the conductive coating 23 on the annular body. Thus, when the needle electrode 20 is in its advanced position as shown in FIG. 4, the RF energy from the generator is supplied between the needle electrode 20 and the conductive coating 23, allowing the needle to perform the electrosurgical cutting of tissue adjacent thereto.

The first and second contacts, as constituted by the conductive bushing 27 and the annular ring 28, are provided as before. The chamber 29 is covered with an insulating lining 35 except for the annular ring 28. The annular ring 28 is in electrical contact with the proximal portion of the annular body 13. When the needle electrode is withdrawn into the instrument 10 by the operation of the remote handle, the conductive bushing 27 comes into contact with the annular ring 28, similar to the arrangement shown in FIG. 3. This means that RF energy from the generator 1 is directed from the guide wire 19, through the conductive bushing 27 and annular ring 28 to the annular body 13. The RF energy from the generator is supplied between the conductive coating 23 and the annular body 13, allowing the annular body to perform the electrosurgical coagulation of tissue adjacent thereto.

Other variations can be envisaged without departing from the scope of the present invention. The first, second and third electrodes can be constituted by components of different shapes and sizes, and not merely the needle electrode depicted. The second and third electrodes, whether they be printed patterns 33 & 34 or any other type of electrode, need not necessarily be mounted on a stationary member 11. Alternatively they could conceivably be mounted on movable jaw members, capable of opening and closing to grasp tissue therebetween. Whatever the design of the distal tip of the instrument, the use of the movement of the electrode assembly to make selective contact between the conductive bushing 27 and the annular ring 28 allows for three electrodes to be selectively utilised with only two connections to the generator, in this instance constituted by the guide wire 19 and the flexible conductive tube 15. The need for a third lead extending all the way down the sheath 3 is avoided, and this can give greater simplicity to the design and better reliability, especially where the sheath is several meters in length and relatively small in diameter.

What is claimed is:

1. An electrosurgical instrument for the treatment of tissue, the instrument comprising:
    an instrument shaft having a longitudinal axis;
    an electrode assembly at one end of the shaft, the electrode assembly comprising first, second and third electrodes which are electrically insulated one from another by means of one or more insulation members,
        the instrument further comprising first and second connections by which RF energy can be supplied to the instrument from an electrosurgical generator,
        the first electrode being movable longitudinally between an advanced position in which it extends from the instrument shaft and a retracted position in which it is less advanced with respect to the instrument shaft,
        the instrument being such that when the first electrode is in its advanced position the first and second connections are in electrical communication with the first and second electrodes, and such that the movement of the first electrode to its retracted position causes the first and second connections to be in electrical communication with the second and third electrodes;
    a first electrical communication element located on the first electrode and connected to the said first connection; and
    a second electrical communication element located adjacent the first electrode and connected to the third electrode, the relative positions of the communication elements configured such that movement of the first electrode to its retracted position brings the communication elements together configured to form an electrical path between the first connection and the third electrode.

2. An electrosurgical instrument according to claim 1, wherein, when the first electrode is in its advanced position, the first connection is in electrical communication with the first electrode and the second connection is in electrical communication with the second electrode, and when the first electrode is in its retracted position, the first connection is in electrical communication with the third electrode and the second connection is in electrical communication with the second electrode.

3. An electrosurgical instrument according to claim 1, wherein the first electrode is adapted to perform the electrosurgical cutting of tissue.

4. An electrosurgical instrument according to claim 3, wherein the first electrode is a needle electrode.

5. An electrosurgical instrument according to claim 1, wherein the first electrode is located in a lumen extending longitudinally through the electrosurgical instrument.

6. An electrosurgical instrument according to claim 1, wherein the first electrode is such that it is completely contained within the instrument shaft when in its retracted position.

7. An electrosurgical instrument according to claim 1, wherein the second and third electrodes are adapted to perform electrosurgical coagulation of tissue.

8. An electrosurgical instrument according to claim 1, wherein the instrument includes an annular body surrounding the first electrode.

9. An electrosurgical instrument according to claim 8, wherein the second and third electrodes comprise first and second printed patterns present on the annular body.

10. An electrosurgical instrument according to claim 8, wherein the annular body is electrically conductive and constitutes the third electrode.

11. An electrosurgical instrument according to claim 8, wherein the second electrode comprises an electrically conductive layer on at least part of the annular body, an electrically insulating layer being present between the annular body and the conductive layer.

12. An electrosurgical instrument according to claim 1, including first and second electrical contacts, the first contact being in electrical connection with the first electrode and the second contact being in electrical connection with the third electrode.

13. An electrosurgical instrument according to claim 12, wherein the first contact is carried on the first electrode.

14. An electrosurgical instrument according to claim 12, wherein the first and second contacts are such that they are not in electrical contact when the first electrode is in its advanced position.

15. An electrosurgical instrument according to claim 14, wherein the first and second contacts are such that they are in electrical contact when the first electrode is in its retracted position.

16. An electrosurgical instrument for the treatment of tissue, the instrument comprising:
   an instrument shaft having a longitudinal axis, and
   an electrode assembly at one end of the shaft, the electrode assembly comprising first, second and third electrodes which are electrically insulated one from another by means of one or more insulation members,
   the instrument further comprising first and second connections by which RF energy can be supplied to the instrument from an electrosurgical generator,
   the first electrode being movable longitudinally between an advanced position in which it extends from the instrument shaft and a retracted position in which it is less advanced with respect to the instrument shaft, wherein
   the instrument further comprises:
      associated with the distal end of the instrument shaft, a pair of electrical coupling elements the relative position of the coupling elements is caused to alter by movement of the first electrode between its advanced and retracted positions thereby to form an electrical coupling such that when the first electrode is in its advanced position the first and second connections are in electrical communication with the first and second electrodes, and when the first electrode is in its retracted position the first and second connections are in electrical communication with the second and third electrodes, the coupling elements comprising:
      a first coupling element located on the first electrode and coupled to said first connection, and
      a second coupling element located adjacent the first electrode and coupled to the third electrode, the relative positions of the coupling elements configured such that movement of the first electrode to its retracted position brings the coupling elements together configured to form an electrical path between the first connection and the third electrode.

17. An electrosurgical instrument according to claim 16, wherein the first electrode and the third electrode each have respective electrical contacts forming said coupling elements, which contacts engage each other when the first electrode is retracted.

* * * * *